United States Patent
Nagai et al.

(10) Patent No.: US 8,158,060 B2
(45) Date of Patent: Apr. 17, 2012

(54) SAMPLE ANALYZER AND SAMPLE CONTAINER SUPPLYING APPARATUS

(75) Inventors: Takaaki Nagai, Kobe (JP); Mitsuo Yamasaki, Kobe (JP)

(73) Assignee: Sysmex Corporation, Kobe (JP)

( * ) Notice: Subject to any disclaimer, the term of this patent is extended or adjusted under 35 U.S.C. 154(b) by 1002 days.

(21) Appl. No.: 11/599,790

(22) Filed: Nov. 15, 2006

(65) Prior Publication Data

US 2007/0110617 A1 May 17, 2007

(30) Foreign Application Priority Data

Nov. 15, 2005 (JP) ................................. 2005-330497

(51) Int. Cl.
*G01N 35/02* (2006.01)
*G01N 35/10* (2006.01)

(52) U.S. Cl. ............ 422/65; 422/63; 422/501; 422/562; 436/47; 436/48; 436/49

(58) Field of Classification Search .................. None
See application file for complete search history.

(56) References Cited

U.S. PATENT DOCUMENTS

| | | | |
|---|---|---|---|
| 5,735,387 A * | 4/1998 | Polaniec et al. ............ 198/690.1 |
| 6,255,614 B1 * | 7/2001 | Yamakawa et al. ............ 209/587 |
| 6,790,413 B2 * | 9/2004 | Ngo et al. ........................ 422/65 |
| 6,818,182 B2 | 11/2004 | Le Comte et al. |
| 7,392,949 B2 | 7/2008 | Itoh |
| 2005/0186113 A1* | 8/2005 | Koike et al. ..................... 422/63 |
| 2006/0210438 A1 | 9/2006 | Nagai et al. |
| 2007/0048185 A1* | 3/2007 | Dupoteau et al. ............ 422/68.1 |
| 2007/0189926 A1* | 8/2007 | Le Comte ........................ 422/65 |
| 2008/0318306 A1 | 12/2008 | Le Comte et al. |

FOREIGN PATENT DOCUMENTS

| | | |
|---|---|---|
| CN | 1680967 A | 10/2005 |
| CN | 1834659 A | 9/2006 |
| WO | WO 2005/022168 * | 3/2005 |
| WO | WO 2005/101024 * | 10/2005 |
| WO | WO 2005/101025 A1 | 10/2005 |

OTHER PUBLICATIONS

Chinese Office Action for Chinese Application No. 200610138140.0, dated Sep. 18, 2009, 2 pages.

* cited by examiner

*Primary Examiner* — P. Kathryn Wright
(74) *Attorney, Agent, or Firm* — Brinks Hofer Gilson & Lione

(57) ABSTRACT

A sample analyzer for analyzing a sample comprising: a sample container receiver capable of receiving either one of a manually supplied sample container and an automatically supplied; a container holder receiver for receiving a container holder holding at least one sample container; a sample container supplier automatically for supplying, to the sample container receiver, a sample container held by the container holder received by the container holder receiver; an aspirator for aspirating a sample within a sample container received by the sample container receiver; and an analyzing part for analyzing the sample aspirated by the aspirator.

4 Claims, 14 Drawing Sheets

SAMPLE ANALYZER AND SAMPLE CONTAINER SUPPLYING APPARATUS

This application claims priority under 35 U.S.C. §119 to Japanese Patent Application No. JP2005-330497 filed Nov. 15, 2005, the entire content of which is hereby incorporated by reference.

FIELD OF THE INVENTION

The present invention relates to a sample analyzer and sample container supplying apparatus.

BACKGROUND OF THE INVENTION

Sample analyzers include, for example, blood analyzers. Such sample analyzers aspirate a sample such as blood or the like collected in a sample container (collection tube), mix the aspirated sample with reagent, the mixed sample is measured by a measuring device, and the measurements are analyzed to obtain analysis results.

Sample analyzers are generally provided with an automatic sample container supplying apparatus efficiently process the samples collected in a large number of sample containers. In the case of a sample analyzer provided with the automatic sample container supplying apparatus, when an operator sets a plurality of sample containers in the automatic sample container supplying apparatus, the plurality of sample containers are sequentially and automatically transported to the sample aspirator where they are aspirated. Thus, the operator need not set the sample containers one by one in the sample analyzer.

An example of an apparatus having this function is the blood product sample processing device disclosed in U.S. Pat. No. 6,818,182. This device for processing samples of blood products is provided with a sampling means capable of collecting blood product samples contained in tubes loaded in a cassette, and a moving means for transferring the cassette loaded with the tubes that contain the blood products.

The blood product sample processing device is further provided with a loading means for manually loading a tube containing a blood product. This manual loading means is disposed near the moving means and holds at least one tube, and when there is no cassette present, that tube is disposed within the path of the moving means and sampling means so as to allow the sample to be collected by the sampling means. Thus, a tube other than a tube loaded in a cassette can be manually loaded and aspirated by the sampling means.

Moreover, the manual loading means is configured so as to rotate and incline when a tube is manually loaded, and the manual loading means is rotated when a tube is disposed within the path of the moving means and sampling means.

Disadvantages of the above processing device are the complexity and large size of the apparatus. In this processing device, for example, the sampling means for aspirating a sample (aspirator) both aspirates a sample from a tube set in a cassette that has been moved to a predetermined position by the moving means, and aspirates a sample from a tube that has been loaded in the manual loading means. Therefore, the mechanism of the sample means is more complex and larger in size due to the requirement of aspiration in the above two instances.

SUMMARY OF THE INVENTION

The scope of the present invention is defined solely by the appended claims, and is not affected to any degree by the statements within this summary.

A first aspect of the sample analyzer of the present invention is a sample analyzer for analyzing a sample comprising: a sample container receiver capable of receiving either one of a manually supplied sample container and an automatically supplied; a container holder receiver for receiving a container holder holding at least one sample container; a sample container supplier automatically for supplying, to the sample container receiver, a sample container held by the container holder received by the container holder receiver; an aspirator for aspirating a sample within a sample container received by the sample container receiver; and an analyzing part for analyzing the sample aspirated by the aspirator.

A second aspect of the sample analyzer of the present invention is a sample analyzer for analyzing a sample comprising: a casing; a sample container receiver that receives a sample container in an substantial upright state at a predetermined receiving position which is outside the casing; an aspirator provided within the casing for aspirating a sample within a sample container received by the sample container receiver and disposed at a predetermined aspirating position within the casing; an analyzing part for analyzing the sample aspirated by the aspirator; and a moving part for moving the sample container received by the sample container receiver from the receiving position to the aspirating position.

A third aspect of the sample analyzer of the present invention is a sample analyzer, detachably connected to a container supplying apparatus, comprising: a sample container receiver for receiving a sample container; an aspirator for aspirating a sample within the sample container received by the sample container receiver; an analyzing part for analyzing the sample aspirated by the aspirator; and a moving part for moving the sample container receiver to an aspirating position at which the aspirator aspirates a sample, a first container receiving position for receiving a sample container manually supplied, and a second container position for receiving a sample container automatically supplied by the sample container supplying apparatus.

A fourth aspect of the sample container supplying apparatus of the present invention is a sample container supplying apparatus for supplying a sample container to a sample analyzer comprises a sample container receiver for manually receiving a sample container to aspirate and analyze a sample contained in the sample container, the apparatus comprising: a container holder receiver for receiving a container holder holding at least one sample container; and a sample container supplier for supplying, to the sample container receiver of the sample analyzing main body apparatus, a sample container held by the container holder received by the container holder receiver.

DETAILED DESCRIPTION OF THE PREFERRED EMBODIMENT

The preferred embodiments of the present invention are described hereinafter.

Figure 1:
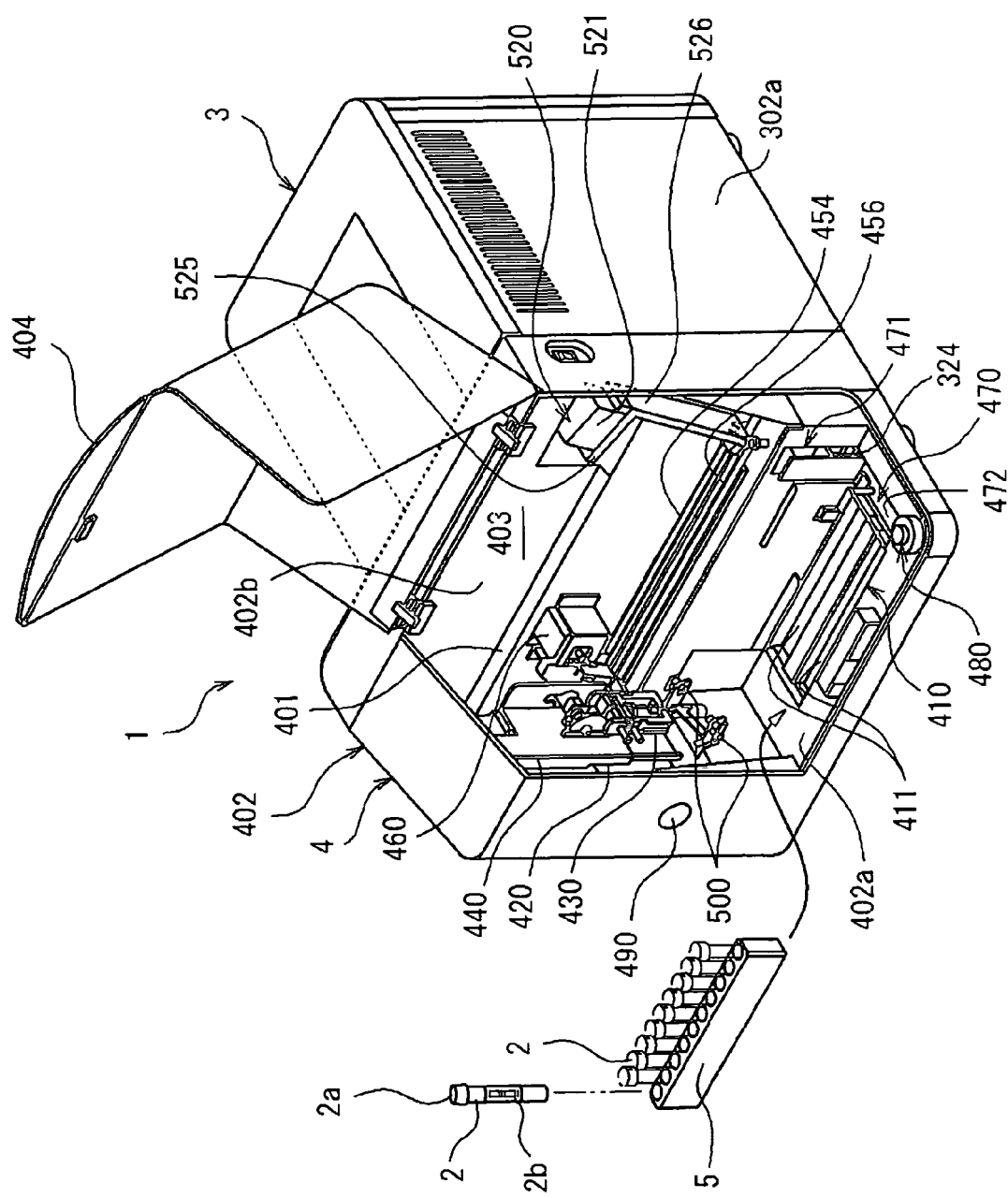
FIG. 1 is a perspective view of a sample analyzer.

FIG. 1 shows a blood analyzer as an example of a sample analyzer 1. The sample analyzer 1 measures a blood sample contained in a sample container (collection tube) 2, and the measurement result is analyzed by a computer 7 (omitted from FIG. 1).

The sample analyzer 1 is provided with a sample analyzer main body apparatus (blood analyzer main body apparatus) 3 with the function of measuring the sample blood, and a sample container supplier (sampler) 4 that automatically supplies a plurality of sample containers to the sample analyzer main body 3.

Figure 2:
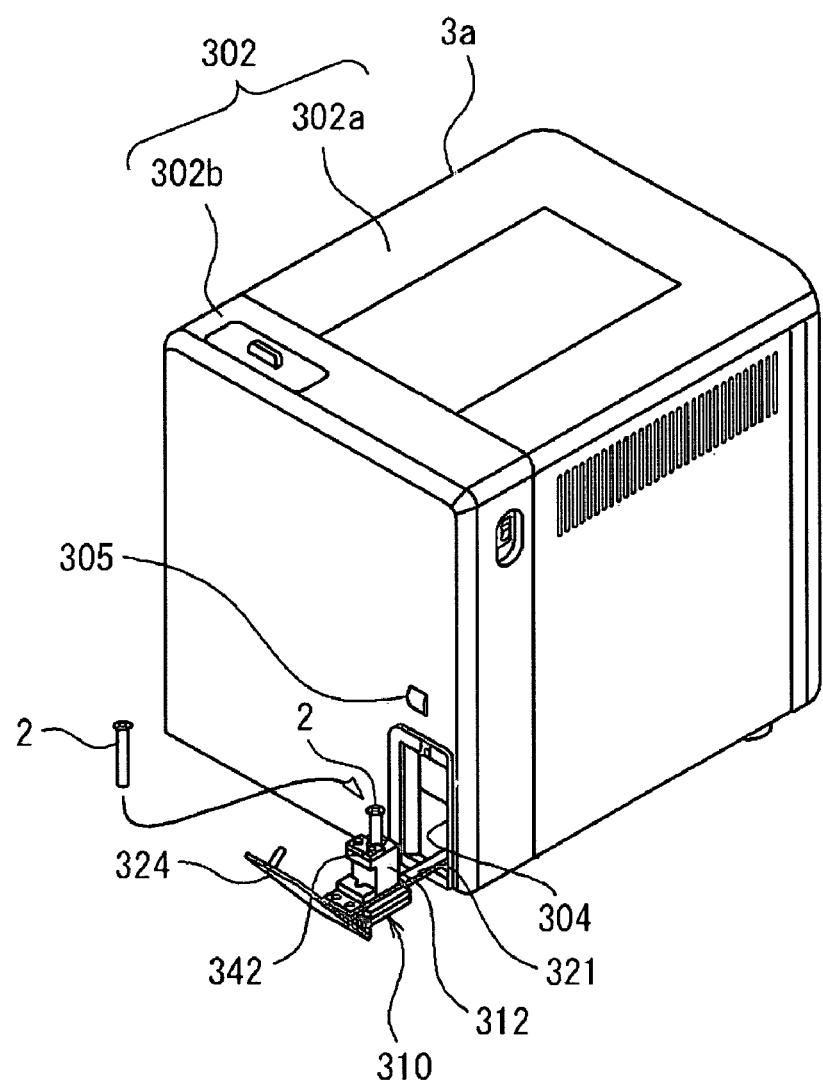
FIG. 2 is a perspective view of the manual placement-type sample analyzer (sample analyzer main body)

As shown in FIG. 2, the sample analyzer main body 3 is originally configured as a manual placement-type sample analyzer 3a that measures a manually placed sample container 2.

Figure 3:
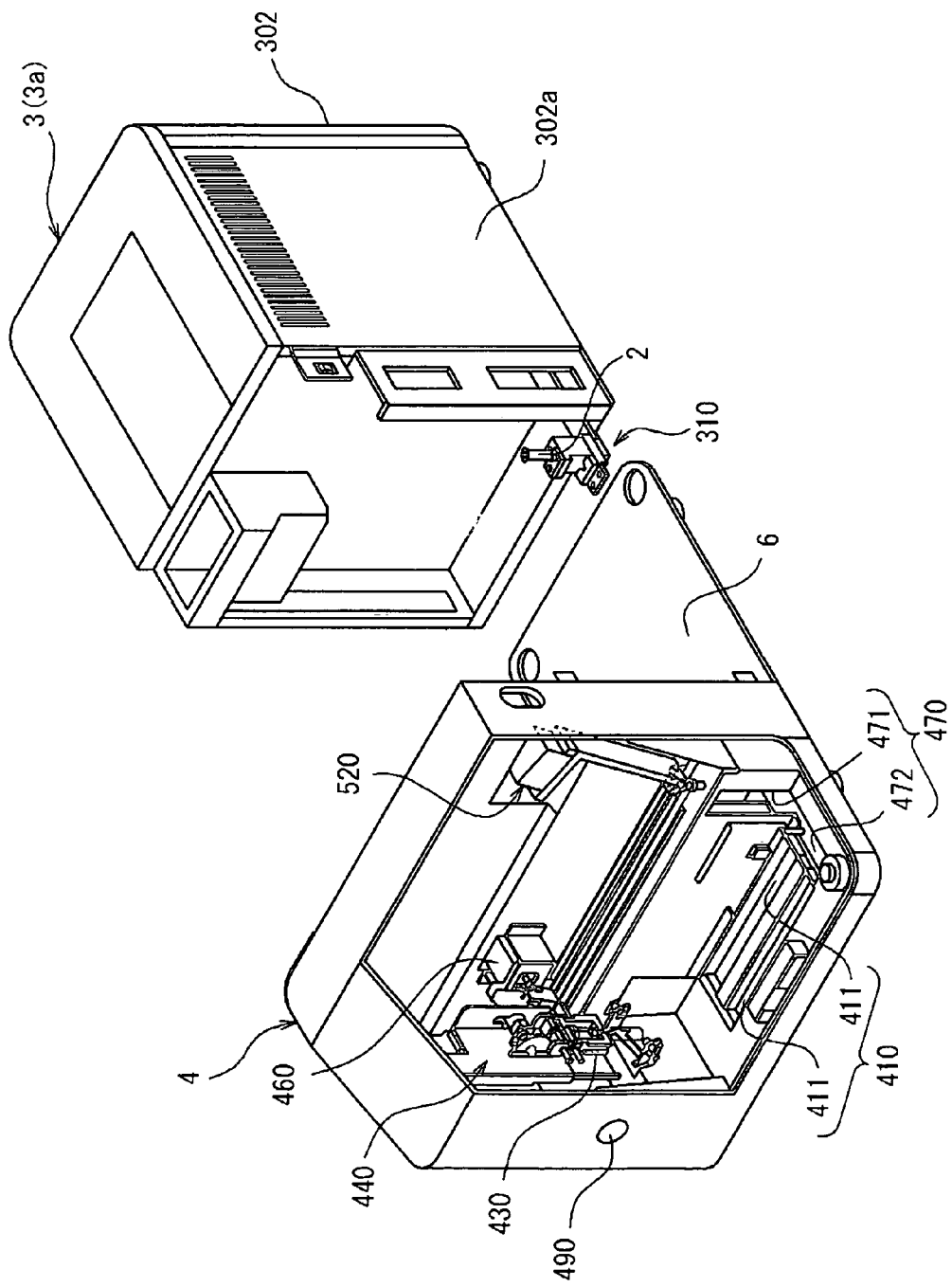
FIG. 3 is an exploded perspective view of the sample analyzer.

The sample analyzer 1 has a sample container supplier 4 subsequently joined to a manual placement-type sample analyzer 3a, as shown in FIG. 3, and the two devices 3a and 4 are integrated so as to be separable, thus configuring a sample analyzer with a detachable sampler attachment. As a result, the sample analyzer 1 not only allows manual placement of sample containers 2, but also automatically supplies sample containers 2.

Moreover, the two devices 3a and 4 may be integrated after initial assembly of the devices during the manufacturing process.

Sample Analyzer Main Body 3 (Manual Placement-Type Sample Analyzer 3a)

Figure 4:
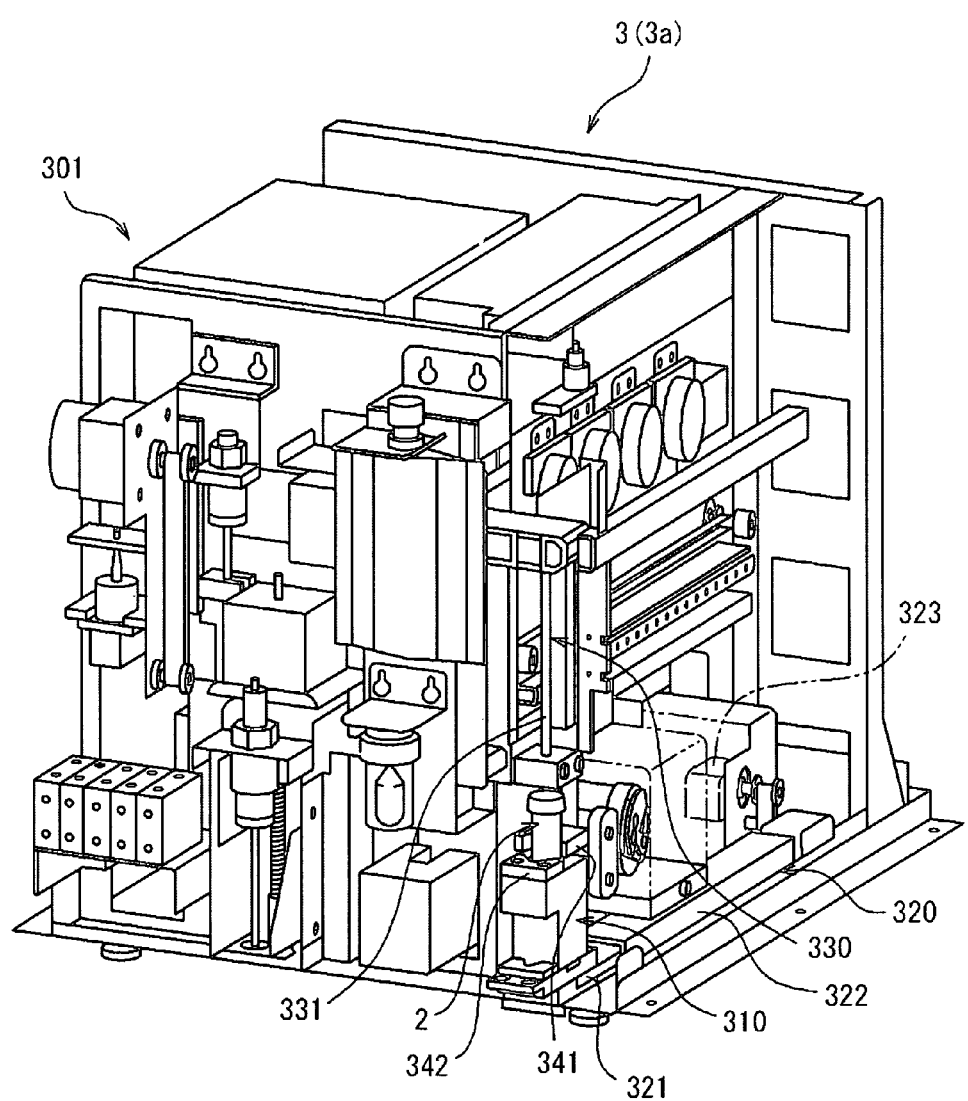
FIG. 4 is a perspective view of the inner mechanism of the manual placement-type sample analyzer.

FIGS. 2 and 4 show the manual placement-type sample analyzer 3a (sample analyzer main body 3). The manual-placement-type sample analyzer 3a is mainly configured by an internal mechanism 301 having a measuring unit for measuring samples and the like, and a casing 302 that houses the internal mechanism unit 301.

The casing 302 is provided with a casing body 302a (refer to FIG. 3) that has an open front (one surface), and a front casing 302b mounted on the casing body 302a so as to obstruct the front opening of the casing body 302a. When the sample container supplier 4 is installed on the sample analyzer main body 3a, the front casing 302b is removed (refer to FIG. 3).

An opening 304 is formed in the bottom right area of the front casing 302b, such that a sample container acceptor 310, in which a sample container 2 is manually set, can move forward from inside the casing 302 to the front of the casing 302 (refer to FIG. 2).

The internal mechanism 301 is provided with a sample container acceptor 310 and a mover 320 that moves the sample container acceptor 310.

The sample container acceptor 310 is provided with a mounting base 312 that has a holding orifice 311 (refer to FIG. 6) for holding a tube-like sample container collection tube in an upright and approximately vertical state. The holding orifice 311 is open at the top, and the hole extends vertically (perpendicular direction). Therefore, setting and replacing a sample container 2 on the sample container acceptor 310 is accomplished by setting and removing the sample container 2 in a vertical direction (perpendicular direction).

Moreover, the holding orifice 311 has a relatively large diameter to allow the insertion of sample containers of various tube diameters.

Figure 5:
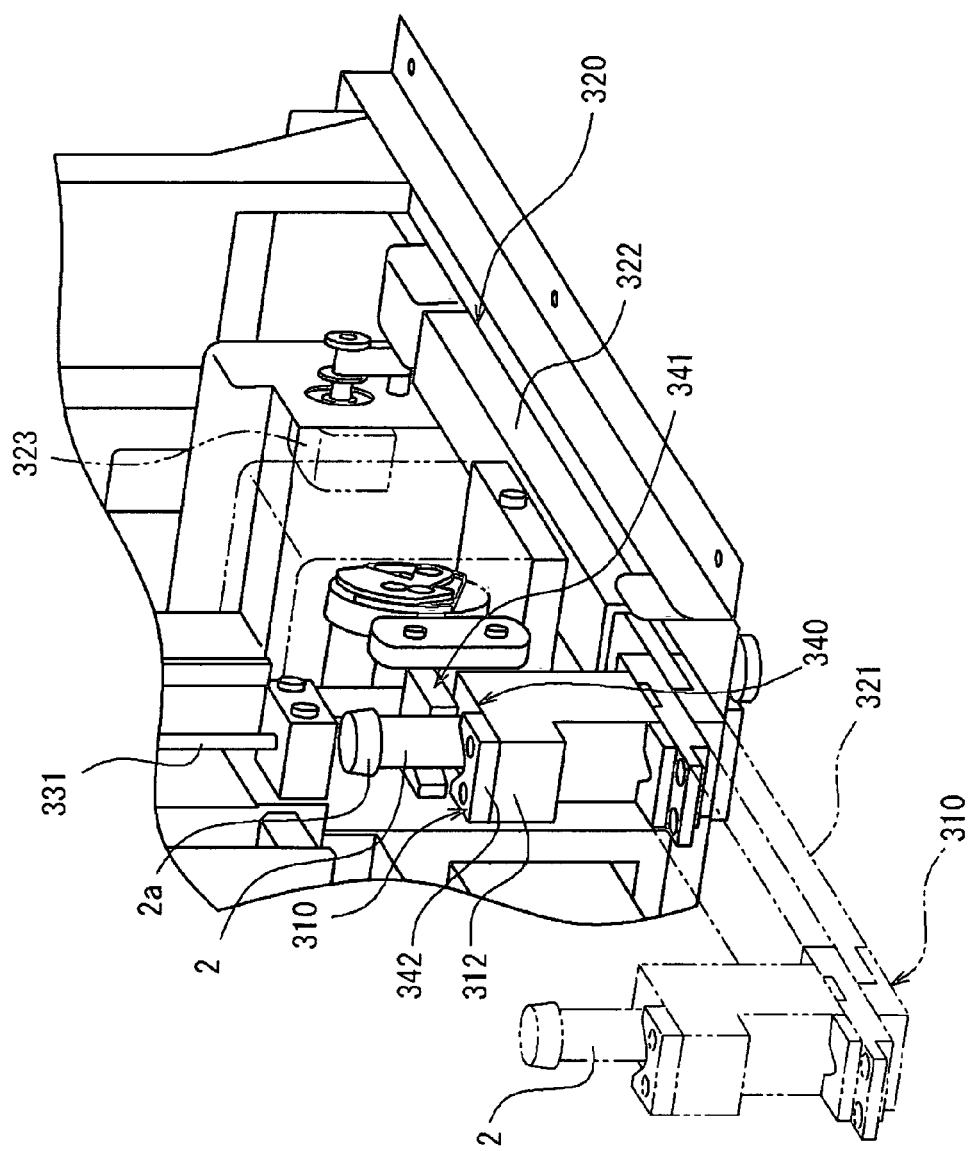
FIG. 5 is an enlarged view of the sample container placement part of the moving unit of the manual placement-type sample analyzer.

The mover 320 is configured so as to move the mounting base 312 in front-to-back directions. As shown in FIG. 5, the mover 320 is provided with a slider 321 that is movable in forward and backward directions and on the leading end of which is mounted the mounting base 312, a guide 322 that guides the forward and backward movement of the slider 321, and a motor 323 that functions as the drive unit that drives the slider 321.

When the motor 323 rotates, the rotational movement is transmitted to the guide 322 side via a belt 324. This rotational movement is converted to a linear movement by a rotation-to-linear movement conversion mechanism not shown in the drawing that is built into the guide 322, such that the slider 321 is moved in forward and backward directions.

Moreover, since the slider 321 is provided so as to move horizontally, a sample container 2 set in an approximately vertical state on the sample receiver 320 can be moved horizontally while maintaining the vertical condition of the sample container.

When the slider 321 is moved forward, the sample container acceptor 310 projects forward from the opening 304, as shown in FIG. 2, such that a sample container 2 can be set in the holding orifice 311. Furthermore, the position of the sample container acceptor 310 shown in FIG. 2 is referred to as the manual sample container receiving position. When the slider 321 is moved backward, the sample container acceptor 310 is housed within the apparatus, as shown in FIG. 4.

A cover 324 used to close the opening 304 is rotatably provided on the end of the slider 321 (refer to FIG. 2). A spring not shown in the drawing exerts a force so as to incline the cover 324 to the outer side at a predetermined angle. When the slider 321 is retracted, the cover 324 is moved from the state shown in FIG. 2 in an upward direction to close the opening 304, and when the slider 321 advances, the cover 324 is moved forward and downward to the state shown in FIG. 2.

A measurement start button 305 is provided on the front of the casing 302. When the start button 305 is pressed after the sample container 2 has been inserted in the holding orifice 311 of the mounting base 312, the slider 321 is retracted, and the sample container 2 (sample receiver 310) is positioned at the aspirating position (the position shown in FIG. 4) within the apparatus 3. Thus, in the manual placement-type sample analyzer 3a, the sample container acceptor 310 moves between the manual sample container receiving position and the aspirating position.

An aspirator 330 is provided within the apparatus 3 to aspirate the sample within the sample container 2 that is disposed at the aspirating position. The aspirator 330 is provided with an aspiration tube 331 that is moved downward (vertically downward direction) and pierces the stopper 2a that seals the sample container 2, then aspirates the sample within the sample container. The aspirator 330 is further provided with a horizontal drive mechanism for moving the aspiration tube 331 horizontally within the apparatus 3, and a vertical drive mechanism for moving the aspiration tube 331 vertically.

The holding orifice 311 of the sample container acceptor 310 is formed relatively large so as to allow the insertion of sample containers of various diameters as previously mentioned. Therefore, there is a possibility that the sample container 2 accommodated in the holding orifice 311 may be somewhat inclined and eccentrically positioned and leaning within the holding orifice 311. There is concern that the inclination, eccentricity and leaning of the sample container may hinder the aspiration tube 331 as it advances within the sample container 2.

In the present embodiment, a positioning part 340 is provided to position the sample container 2 so as to prevent the sample container from leaning at the aspirating position.

Figure 6:
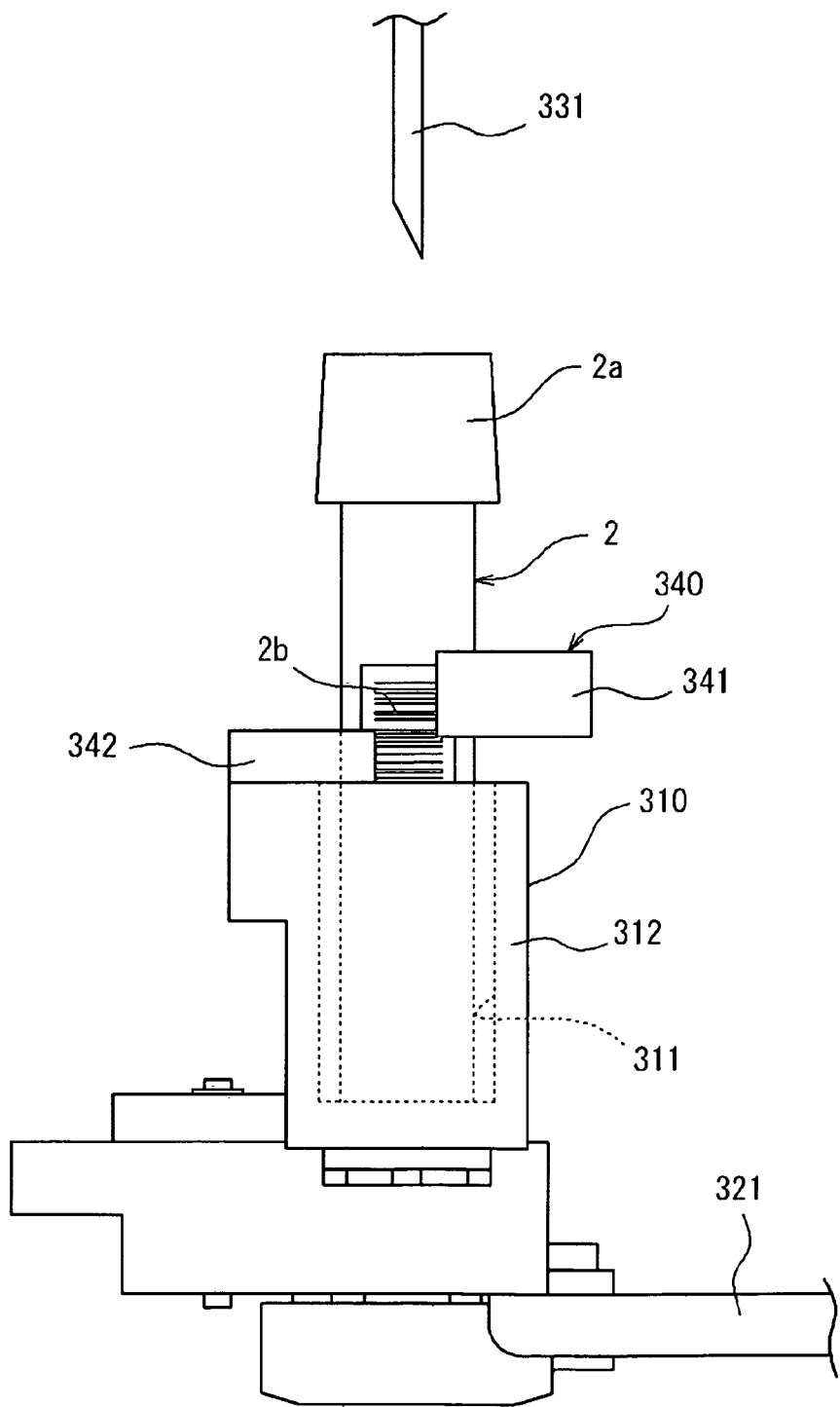
FIG. 6 is a side view of the sample container positioner.

As shown in FIGS. 5 and 6, the positioning part 340 is configured by a stationary positioner 341 provided at a fixed position within the apparatus 3, and a movable positioner 342 provided on the sample container acceptor 310 side, so as to fix the position of a sample container by holding the sample container 2 between both positioners 341 and 342.

The movable positioner 342 is provided at the top of the mounting base 312, and abuts the front side of a sample container 2 inserted in the holding orifice 311. When the sample container acceptor 310 is retracted to the aspirating position, the back side of the sample container 2 abuts the stationary positioner 341, and the sample container 2 is gripped from the front and back by the stationary positioner 341 and the movable positioner 342. Thus, the sample container 2 is held stable and stationary, and ensures reliable aspiration of the sample.

Figure 7:
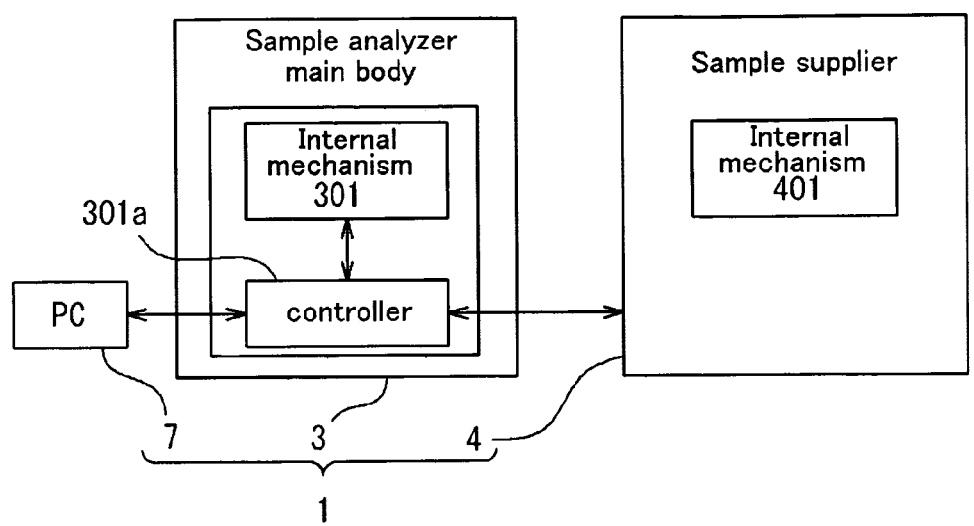
FIG. 7 is a function block diagram of the sample analyzer.

The sample aspirated by the aspirator 330 is mixed with reagent and transported to the measuring unit. For this measuring process, the internal mechanism 301 of the apparatus 3 is provided with a measurement sample preparing unit configured by a reagent containers containing reagent, reagent supply pump, reagent supply path, and mixing chamber for mixing the sample and reagent, and further provided with a controller 301a for controlling the mechanism 301, and a measuring unit for performing measurements related to red blood cells, white blood cells and platelets in the sample prepared by the measurement sample preparing unit (refer to FIG. 7).

Furthermore, the controller is connected to a computer 7 that performs analysis processing of the measurement results, operations of the apparatus and the like, sends measurement result data to the computer, and receives operation instructions from the computer 7.

When the sample container supplier 4 is installed in the apparatus 3, the controller 301a controls the sample container supplier 4.

Sample Container Supplier 4

Figure 8:
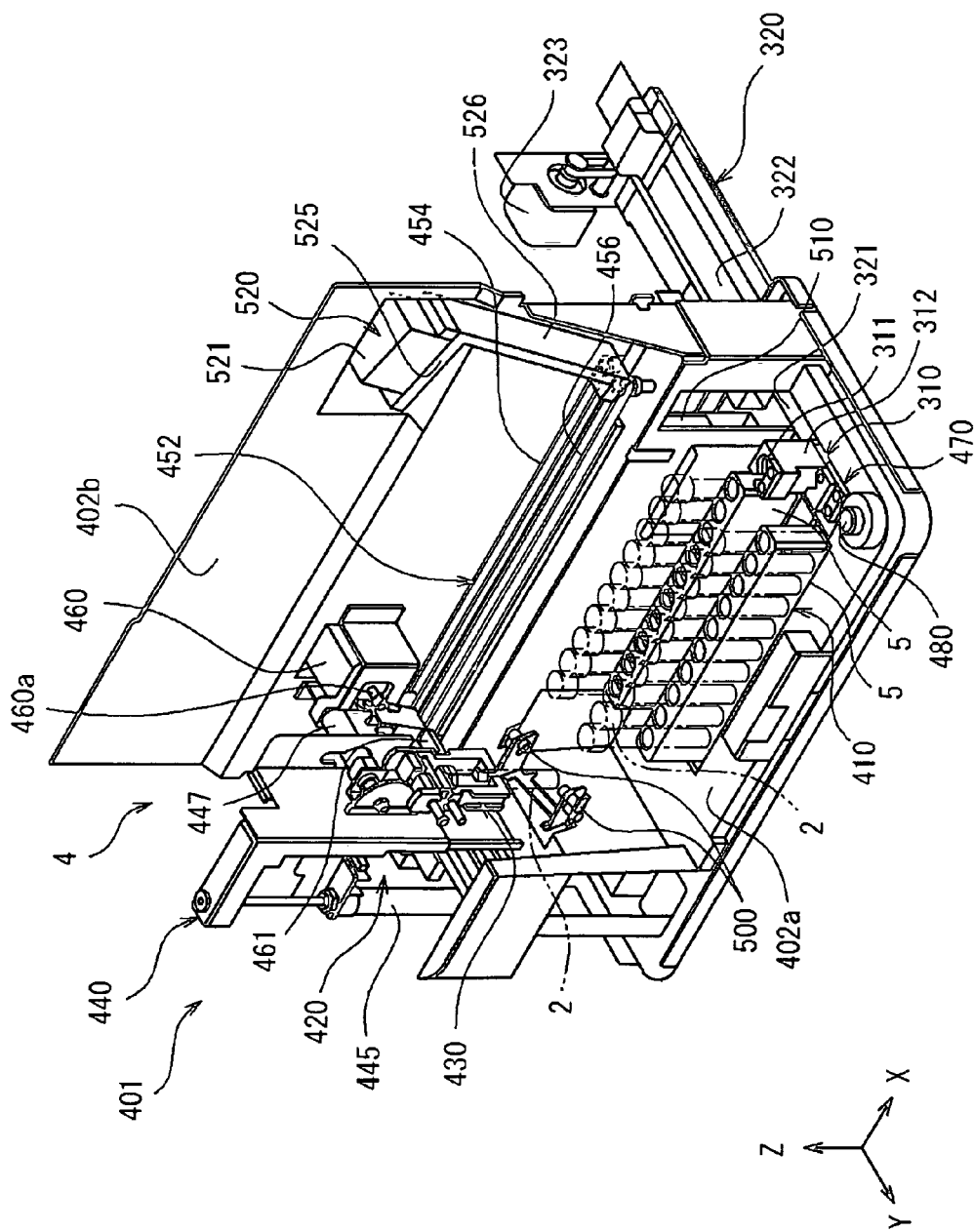
FIG. 8 is a perspective view of the inner mechanism of the sample container supplier.

When a rack 5 holding a plurality of sample containers 2 is set in the sample container supplier 4 shown in FIGS. 3 and 8, the sample container supplier 4 automatically removes the sample container 2 in the rack 5 and supplies the sample container 2 to the sample analyzer main body 3.

The sample container supplier 4 is provided with an internal mechanism 401 for supplying sample containers, and a casing 402 disposed within the internal mechanism 401. Furthermore, FIG. 8 shows the bottom surface 402a and rear surface 402b of the casing 402 with the casing 402 removed.

To facilitate understanding, FIG. 8 also shows the sample container acceptor 310 and moving unit 320 of the sample analyzer main body 3.

As shown in FIG. 3, when the sample container supplier 4 is installed in the manual placement-type sample analyzer 3a (sample analyzer main body 3), the front casing 302b of the apparatus 3 is removed and the sample container supplier 4 is inserted in the front (one side) of the apparatus 3. Furthermore, a mounting plate 6 spans bottom surfaces of both the apparatuses 3 and 4 and is affixed to each by screw or the like, such that both apparatuses 3 and 4 are rigidly coupled.

When the apparatuses 3 and 4 are combined, connective wiring and tubing are required between the apparatuses 3 and 4. For example, the apparatuses 3 and 4 are connected by a power cable for supplying electric power to the electric motor provided in the sample container supplier 4, control signal line allowing the same electric motor to be controlled by the controller 301a of the apparatus 3, air tube for supplying air to the air cylinder provided in the apparatus 4, sensor signal lines for transmitting signals from sensors provided in the apparatus 4 to the controller 301a of the apparatus 3 and the like.

Furthermore, the controller 301a of the apparatus 3 is switchable from a setting for controlling the operation in the manual mode by the apparatus 3, to a setting to control the operation in both the manual mode and the automatic mode.

Rack Holder 410

The bottom surface 402a of the casing 402 is provided with the rack holder 410 in which the rack 5 is set. The rack holder 410 is capable of holding two (multiple) racks 5 equally spaced in front and back. More specifically, arranged on the casing bottom surface 402a of the rack holder 410 are concavities 411 whose lengths extend laterally and are disposed at equal spacing at front and back. A rack sensor (not shown in the drawing) for detecting the presence of the rack 5 in the rack holder 410 is provided on the casing 402, such that automatic operation for supplying a sample container cannot be performed when are rack 5 is not disposed in the rack holder 410.

An opening 403 is formed on the front surface, right side surface and top surface of the casing 402. Furthermore, an openable cover 404 is mounted on the casing 402 to open and close the opening 403. As shown in FIG. 1, when the cover 404 is open, it is possible to set the rack 5 in the rack holder 410 within the casing 402.

Moreover, although the cover 404 is closed during the sample container automatic supplying operation, the cover 404 is formed of a transparent or semi transparent material to allow visual monitoring of the interior through the cover 404.

Sample Container Supplying Unit 420

The sample container supplier 4 is provided with a sample container supplying unit 420 as one mechanism configuring the internal mechanism 401, and which removes the sample container 2 from the rack 5 in the rack holder 410 and moves the sample container 2 to the sample analyzer main body 3 side.

The sample container supplying unit 420 is provided with a moving base 440 (refer to FIG. 9) having a hand-like holder 430 for holding the sample container 2, and a moving part 450 (refer to FIG. 10) that moves the moving base 440 within the apparatus 4.

Moving Base 440

Figure 9:
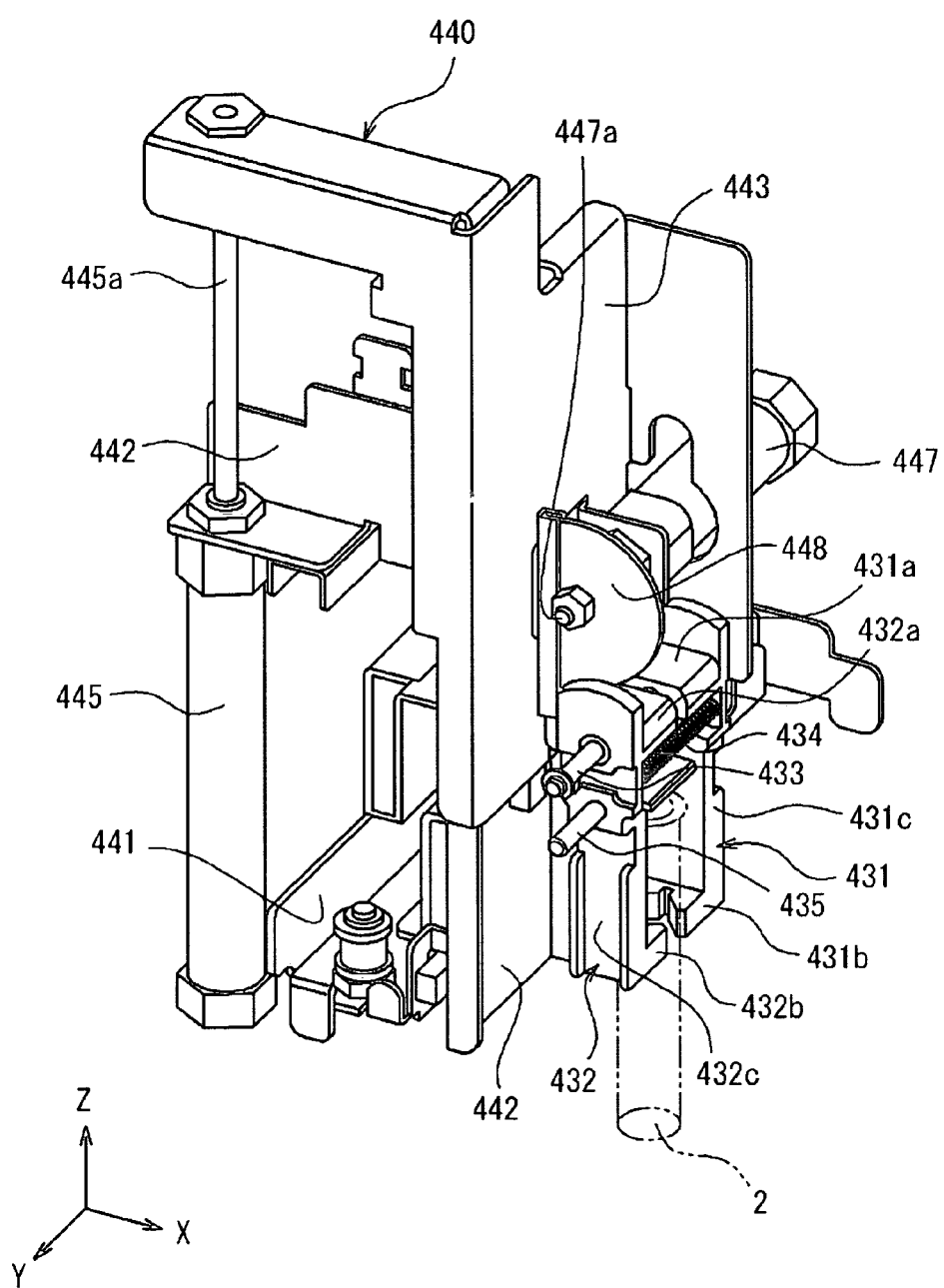
FIG. 9 is a perspective view of the moving base.

As shown in FIG. 9, the moving base 440 is provided with a base body 441, a forward-and-back moving base 442 that is movable in forward-and-backward directions (Y direction in FIG. 9) relative to the base body 441, and an elevator base 443 that is movable in vertical directions (Z direction in FIG. 9) relative to the forward-and-back movable base 442. The elevator base 443 is movable in forward-and-back and vertical directions as viewed from the base body 441.

Furthermore, the holder 430 is mounted on the elevator base 443.

An elevator drive unit (elevator cylinder) 445 that configures the elevator is mounted on the forward-and-back movable base 442. The elevator base 443 is mounted on the leading end of a rod 445a of the elevator cylinder 445. Thus, the elevator base 443 and holder 430 can be raised and lowered relative to the forward-and-back movable base 442 via the extension and retraction of the elevator cylinder 445.

Moving Unit 450

The moving unit 450 moves the movable base 440 laterally (X direction in FIG. 10), and moves the forward-and-back movable base 442 of the movable base 440 in the forward-and-back directions (Y direction in FIG. 10) relative to the base body 441.

Figure 10:
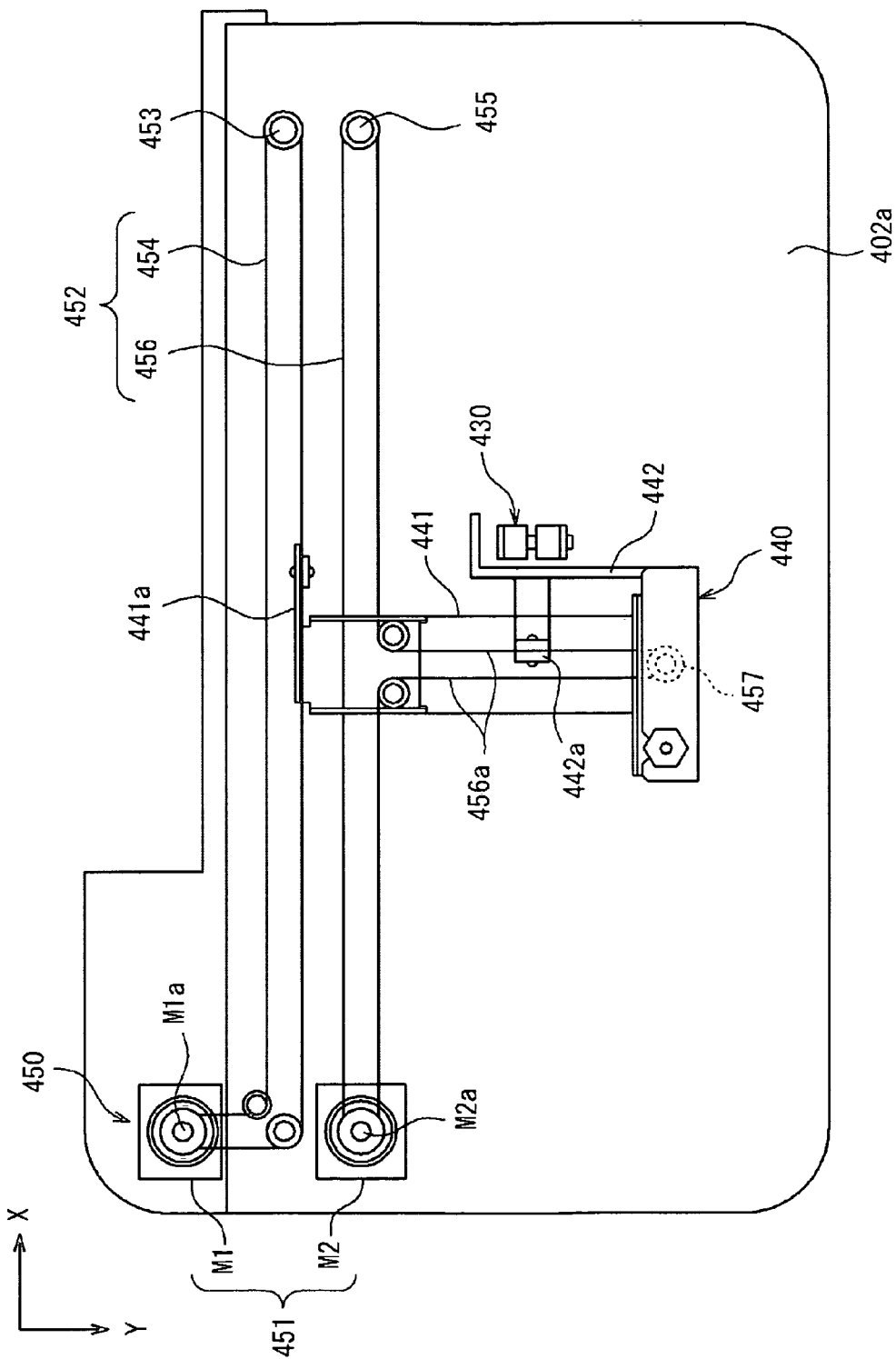
FIG. 10 is a plan view of the moving unit of the sample container supplier.

As shown in FIG. 10, the moving unit 450 is provided with a movement drive unit 451 configured by electric motors M1 and M2, and a transmission mechanism 452 for transmitting the drive force of the movement drive unit to the movable base 440 side.

The first motor M1 of the movement drive unit 451 is disposed on the left side of the interior of the casing 402 of the sample container supplier.

A first belt 454 configuring the transmission mechanism 452 is looped between a rotating shaft M1a of the first motor M1 and a first pulley 453 disposed on the right side of the interior of the casing 402 of the sample container supplier. The first belt 454 extends in a lateral direction at a position at the rear of the interior of the casing 402 of the sample container supplier.

Moreover, the second motor M2 of the movement drive unit 452 is disposed to the front of the first motor M1 and at the left side of the interior of the casing 402 of the sample container supplier. A second belt 456 configuring the transmission mechanism 452 is looped between a rotating shaft M2a of the second motor M2 and a second pulley 455 disposed on the right side of the interior of the casing 402 of the sample container supplier. The second belt 456 also extends in a lateral direction at a position on the front side of the first belt 454 and positioned at the rear of the interior of the casing 402 of the sample container supplier. Furthermore, the second belt 456 is also looped around a third pulley 457 provided on the base body 441 of the moving base 440, and has a part 456a that extends in the front-to-back direction so as to form an T-shape overall.

The base body 441 of the movable base 440 is mounted via a mounting stay 441a on a part extending at the front side of the first belt 454, such that when the first belt 454 is moved laterally via the rotation of the first motor M1, the base body 441 is pulled and the entire movable base 440 is moved laterally.

Furthermore, when the movable base 440 is moved laterally, the second motor M2 also rotates to move the front-to-back movable base 442 forward and back.

The front-to-back movable base 442 of the movable base 440 is mounted via a mounting stay 442a on the right side of the front-to-back extension 456a of the second belt 456, such that the front-to-back movable base 442 is moved in front-to-back directions relative to the base body 441 when the second motor M2 is rotated while the rotation of the first motor M1 is stopped.

According to this configuration, the holder 430 provided on the movable base 440 is movable in lateral directions (direction) front-to-back directions (Y direction), and vertical directions (Z direction) within the apparatus casing 402. That is, the holder 430 can be moved in three-dimensional directions (XYZ directions) via the holder moving mechanisms included in the moving unit 450 and elevator drive unit 445.

Holder 430

Returning to FIG. 9, the holder 430 provided on the movable base 440 (specifically, the elevator base 443) is configured by a pair of finger-like grabbers 431 and 432 that can open and close.

The grabbers 431 and 432 are provided to as to be rotatable on a shaft 433 provided on the elevator 445. The holder 430 is capable of performing a mixing operation, which is described later, by means of the grabbers 431 and 432 provided so as to be rotatable on the shaft 433. The holder 430 faced downward due to its own weight when the mixing operation is not performed. The rotation of the holder 430 is regulated by the attraction of a magnet (not shown in the drawing) provided on the movable base 450 to prevent unnecessary rotation when the mixing operation is not performed.

The grabbers 431 and 432 are provided with bases 431a and 432a that have holes through which the shaft 433 is inserted, and grabber bodies 431c and 432c that have grippers 431b and 432b extending from the bases 431a and 432a and grip the sample containers 2 by the ends thereof.

The grabber (fixed side grabber) 431 among the two grabbers is prevented from moving in the axial direction of the shaft 433. Furthermore, the other grabber (movable side grabber) 432 is provided so as to be movable in the axial direction of the shaft 433.

A spring 434 is provided between the grabbers 431 and 432, and this spring exerts a force so as to force the movable grabber 432 to make contact with the fixed grabber 431. That is, the grabbers 431 and 432 of the holder 430 are normally closed.

A shaft 435 also is inserted through the grabber bodies 431c and 432c of the grabbers 431 and 432 so as to guide the movement (opening and closing movement) of the movable grabber 432.

Holder Grip Drive Unit 447

A holder grip drive unit (holder operating cylinder) 447 configured by an air cylinder is provided on the elevator base 443 of the movable base 440 to open the holder 430, that is to move the movable grabber 432 relative to the fixed grabber 431. A press plate 448 is mounted on the leading end of a rod 447a of the holder opening/closing cylinder 447 to move the movable grabber 432.

Figure 12:
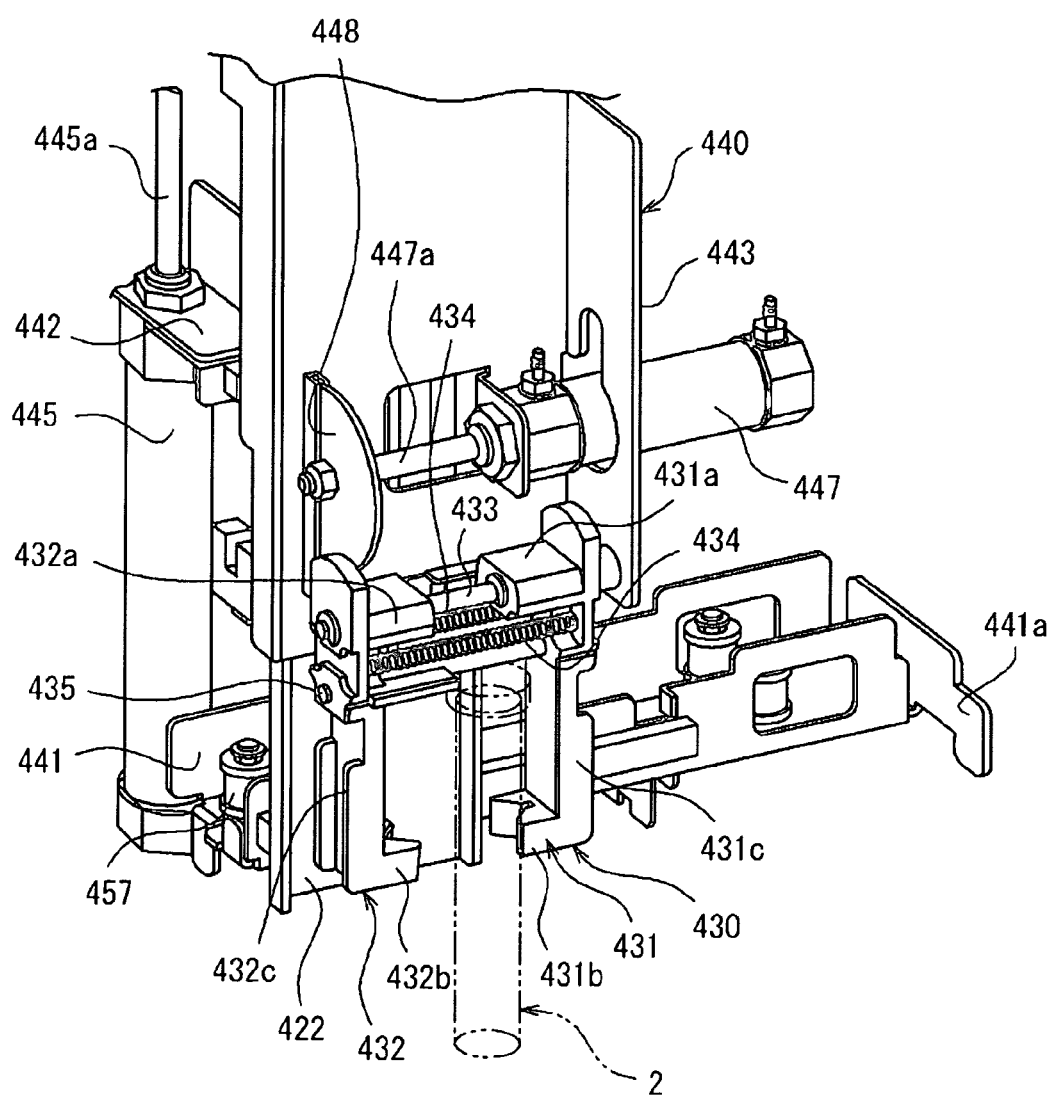
FIG. 12 is a perspective view showing the open state of the holder.

As shown in FIG. 12, when the rod 447a of the holder operating cylinder 447 is extended, the press plate 448 presses the base 432a side of the movable grabber 432, the movable grabber 432 is moved along the shafts 433 and 435, and the holder opens.

When the rod 447a of the holder operating cylinder 447 is contracted, the press plate 448 is separated from the movable grabber 432, the movable grabber 432 is returned via the spring 434, and the holder 430 closes.

When the press plate 448 presses the movable grabber 432 and the holder 430 is open, the rotation of the grabbers 431 and 432 around the shaft 433 is regulated by contact friction between the press plate 448 and the movable grabber 432.

When the holder 430 is closed, however, the press plate 448 separates from the movable grabber 442, and the rotation regulation of the grabbers 431 and 432 by the press plate 448 is released.

Mixing Drive Unit 460

Figure 11:
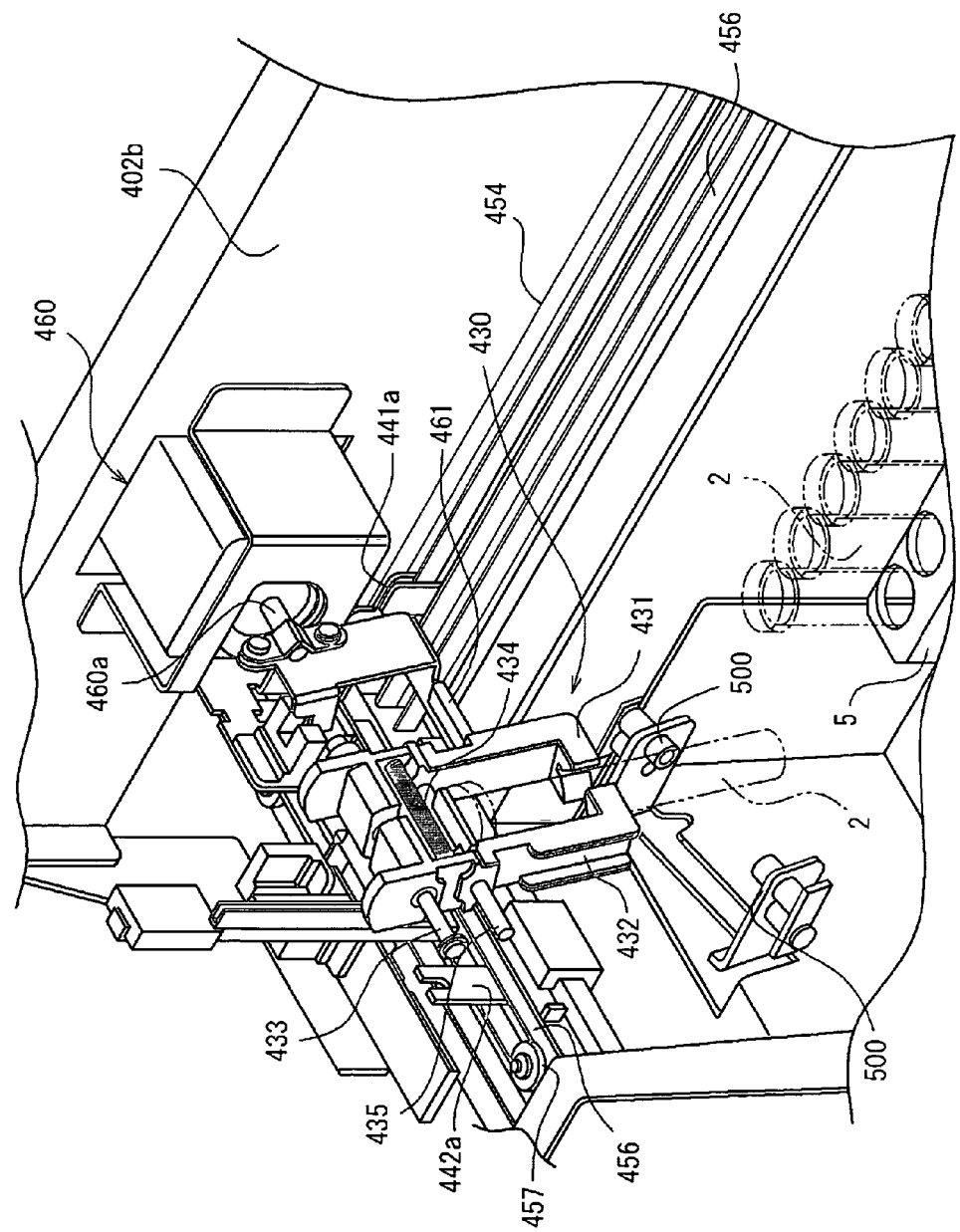
FIG. 11 is a perspective view showing the mixing operation of the holder.

As shown in FIG. 11, a mixing drive unit 460 is provided as an internal mechanism 401 of the apparatus 4 to generate a mixing drive force to mix a sample within the sample container 2 before the sample container 2 is supplied to the sample analyzer main body 3.

The mixing drive unit 460 is configured by an electric motor, and the mixing drive unit 460 is fixedly provided at a position on one side (left side) of the rack holder 410 on the rear surface of the casing 402.

The sides (left side) of the rack holder 410 provided with the mixing drive unit 460 is near the retracted position (movement start position) of the movable base 440 (holder 430).

A contact member 461 is mounted on the rotating shaft 460a of the motor 460 to contact the holder 430 (fixed grabber 431) and transmit the mixing drive force to the holder 430.

The holder 430 hangs down from the shaft 433 due to its own weight. When the movable base 440 is returned to the retracted position by the moving part 450, the contact member 461 of the mixing drive unit 460 contacts the holder 430 in the hanging position. Then, when the motor 460 of the mixing drive unit 460 is rotated one direction, the contact member 461 lifts the holder 430. As a result, the holder 430 is lifted and rotated. Furthermore, when the motor 460 is rotated in the opposite direction, the holder 430 is lowered and rotated via its own weight.

The mixing operation repeats the forward and reverse rotation of the motor 460, by repeatedly raising and lowering the holder 460 that holds the sample container 2. The mixing operation is accomplished by repeating the raising and lowering of the holder 460 approximately ten times. Space is conserved, since the mixing operation is performed at the retracted position of the movable base 440 without the rack 5 of the sample container 2.

Receiver Unit 470 of the Sample Container Acceptor 310

As shown in FIGS. 1 and 3, a receiving unit 470 is provided on the casing 402 of the sample container supplier to receive the arriving sample container acceptor 310 of the sample analyzer main body 3. The receiving unit 470 is provided on the other side (right side) of the rack holder 410 in the lateral direction.

The receiving unit 470 has an opening 471 formed on the bottom right part of the rear surface 402b of the casing 402, and a concavity 472 that accommodates the sample container acceptor 310 that has moved forward and passed through the opening 471 from the sample analyzer main body 3.

The sample container acceptor 310 can advance into the casing 402 of the sample container supplier even when a wall (casing rear surface 402b) separates the sample analyzer main body 3 and the sample supplier 4 via the provision of the opening 471.

Furthermore, the position of the concavity 472 is the position at which the sample container 2 is supplied by the sample supplier 420 (sample container supplying position), and the sample container acceptor 310 can accept the sample container 2 by advancing the sample container acceptor 310 into the concavity 472.

Information Reader (Barcode Reader) 510

Figure 13:
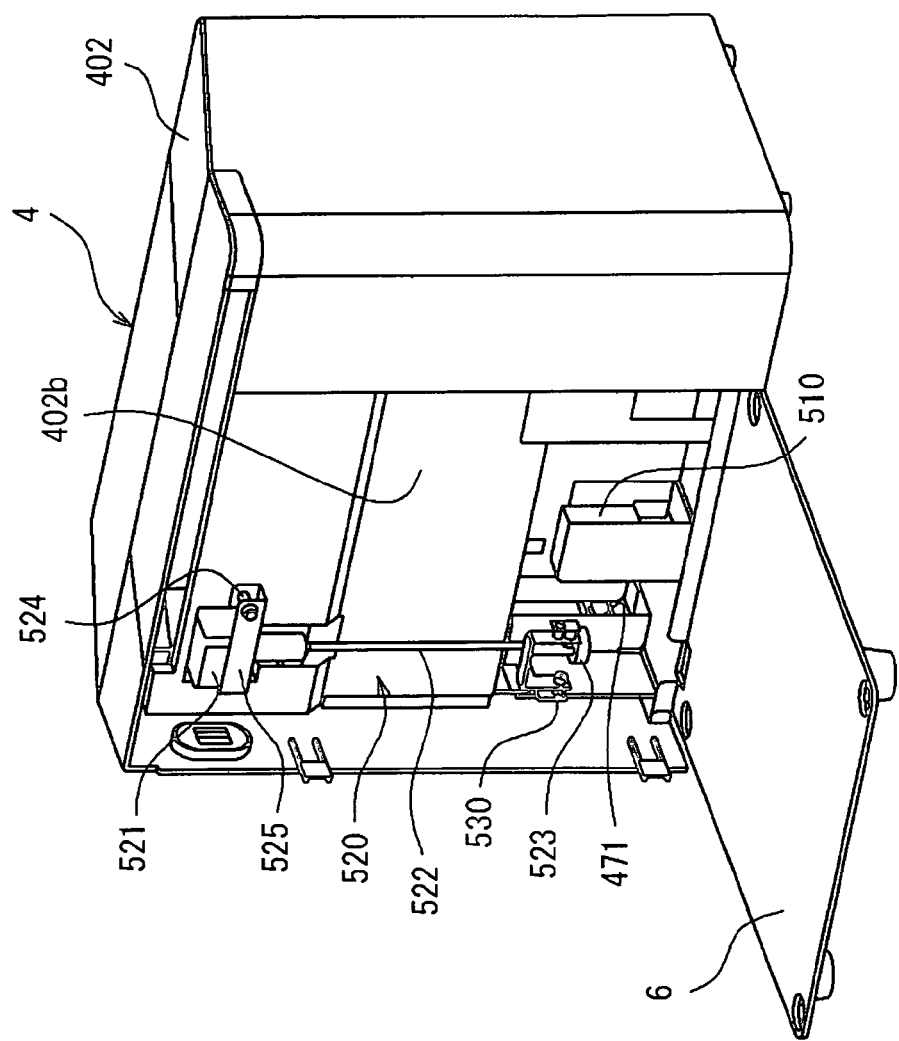
FIG. 13 is a perspective view from the back of the sample container supplier.

As shown in FIG. 13, an information reader 510 for reading the information of an information recording area 2b on the sample container 2 is provided on the back side of the rear surface 402b of the sample container supplier. The information recording area 2b of the sample container 2 is a barcode that records information indicating the identification number of the sample.

The information reader 510 is a barcode reader. The information reader 510 is disposed so as to emit a reading light from the side when the sample container acceptor 310 holding a sample container 2 is retracted from the position of the receiver 470, passes through the opening 403, and is positioned behind the casing rear surface 402b.

The information reading is normally performed by the information reader 510 in the automatic mode when the sample container 2 is supplied by the sample container supplier 4. Since, in the present embodiment, the information of the information recording area 2b is read when the sample container 2 is set in the sample container acceptor 310, information reading can also be performed in the manual mode when the sample container 2 is set manually.

Sample Container 2 Rotation Mechanism 520

As shown in FIG. 13, a rotation mechanism 520 is provided on the rear surface 402b of the casing 402 of the sample container supplier in order to rotate a sample container 2 set at the information reading position around the tube axis. Since the information recording area 2b of the sample container 2 is only present on a part of the tube circumference, the information recording area 2b of a sample tube 2 set at the information reading position may not necessarily be opposite the information reader 510. Therefore, if the sample container 2 is rotated by the rotation mechanism 520, the information recording area 2b can be brought opposite the information reader 510 and the information can be reliably read.

The rotation mechanism 520 is provided with an electric motor 521, rotating shaft 522 extending downward from the motor 521, and a rotation contact 523 provided on the leading end of the rotation shaft 522. The rotation contact 523 abutting the side surface of the sample container 2 rotates the sample container 2 via the rotation of the motor 521.

The motor 521 is supported on the casing rear surface 402b by a support shaft 524. That is, the motor 521 is mounted on a mounting stay 525 supported by the support shaft 424 in a cantilever configuration. Thus, the motor 521 is normally positioned at an inclination from the horizontal, and the rotating shaft 522 is inclined relative to the perpendicular. As a result, the rotation contact 523 is normally positioned apart from the position of the sample container 2 so as to not obstruct the passage of the sample container 2 (refer to the solid line in FIG. 4).

Since the rotation contact 523 contacts the sample container 2, a movable base contact 526 for contacting the movable base 440 is provided on the mounting stay 524 of the rotation mechanism 520.

As can be understood from FIGS. 8 and 13, the motor 521 and mounting stay 525 are disposed so as to pass through the casing rear surface 402b, the movable base contact 526 extends downward on the front side of the casing rear surface 402, and the bottom end of the movable base contact 526 is bent toward the movable base 440 side so as to come into contact with the movable base 440. The movable base contact 526 is also inclined toward the movable base 440 at an inclination similar to the rotating shaft 522.

Figure 14:
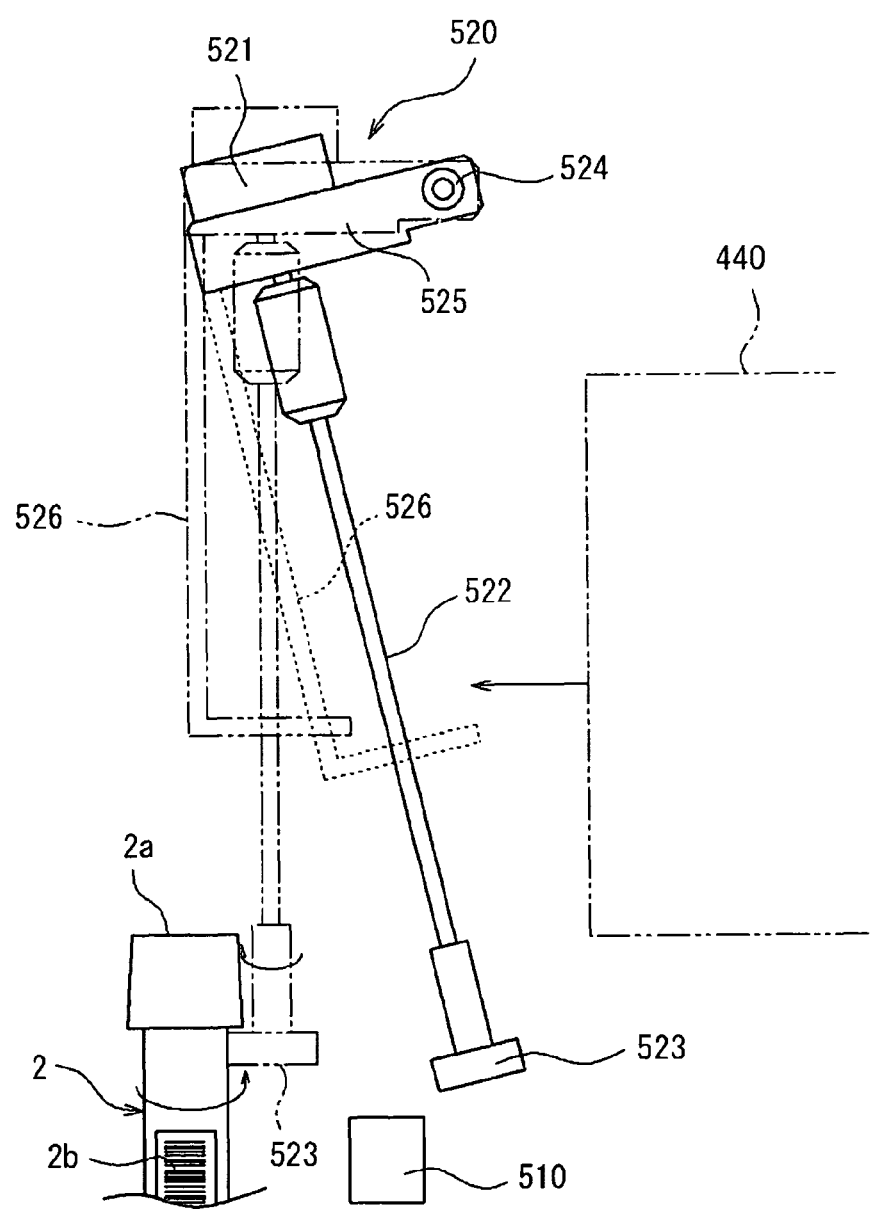
FIG. 14 is a rear view of the rotating mechanism.

When the movable base 440 moves to set the sample container 2 held by the holder 430 in the sample container acceptor 310 (rightward movement; leftward movement viewed from the back surface in FIG. 14) and the movable base 440 contact and pushes the movable base contact 522, the motor 521 and mounting stay 525 rotate upward, and in linkage therewith, the rotating shaft 522 moves to the sample container 2 side and the rotation contact 523 arrives at a position at which it can contact the sample container 2 (refer to the dashed line in FIG. 14).

When the motor 521 is rotated under this condition, the rotation of the rotation contact 522 is transferred to the sample container 2, thus rotating the sample container 2, and information reading can be reliably performed.

Furthermore, when the movable base 440 is moved in a direction separating it from the movable base contact 526, the rotation mechanism 520 naturally returns to the normal position indicated by the solid line in FIG. 14.

Thus, in the present embodiment, the apparatus is simplified since a special drive unit for moving the rotation mechanism 520 can be omitted, and the rotation mechanism 520 can be moved via the movement of the movable base 440.

Sample Container 2 Manual Placement Mode (Manual Mode) in the Sample Analyzer 1

The sequence of the manual mode for setting a sample container 2 manually in the sample analyzer 1 having the previously described configuration is described below.

As shown in FIG. 8, a sample container 2 is inserted in the holding orifice 11 of the sample acceptor 310 when the sample container acceptor 310 is moved forward from the sample analyzer main body 3 and received by the receiver 470 of the sample container supplier 4. When the manual measurement start button 480 provided on the casing bottom surface 402a of the sample container supplier 4, the controller 301a retracts the slider 321. Then, a manually set sample container 2 (sample acceptor 310) is positioned at the aspirating position (position in FIG. 4) of the sample analyzer main body 3.

The sample of the sample container 2 at the aspirating position is aspirated by the aspirator 330, and measured by the measuring unit. Then the measurement results are analyzed by a computer not shown in the drawing.

The manual mode operation, and measurement and analysis processes after placement are basically identical to the sequence in the manually placement mode of the manual placement-type sample analyzer 3a.

In the sample analyzer 1 with the installed sample container supplier 4, the forward extension of the sample container acceptor 310 is greater than the manual placement-type sample analyzer 3a without an installed sample container supplier 4, such that the sample container acceptor 310 can be reliably advanced into the interior of the sample container supplier 4. That is, the sample container supplying position of the sample analyzer 1 is positioned farther forward than the manual sample container setting position in the manual placement-type sample analyzer 3a.

Moreover, the forward extension of the sample container acceptor 310 can be switched by the setting of the controller 301a.

Sample Container 2 Automatic Supplying Operation (Automatic Mode) in Sample Analyzer 1

In the execution of the automatic mode, the rack 5 holding the sample container 2 is set in the rack holder 410, and the cover 404 is closed on the sample container supplier 4, as shown in FIG. 1. The rack 5 holds the sample container 2 in an approximately upright vertical state.

Then, when the automatic measurement start button 490 is pressed, the sample container 2 is automatically supplied and the sample measured. Whether or not the cover 404 is closed is detected by a cover sensor not shown in the drawing; when the cover 404 is not closed, the automatic measurement can not start.

The automatic supply of the sample container 2 is controlled as follows by the controller 301a. First, at the start of the automatic mode, the movable base 440 that has the holder 430 is at the movement start position (retracted position) shown in FIGS. 3 and 8, and the operation starts from this position. The movable base 440 with the holder 430 is moved from the movement start position to the position of the sample container 2 to remove one of the two sample containers 2 in the rack 5 set in the rack holder 410.

When the holder 430 is positioned above the sample container 2 to be removed, the holder 430 is opened and the holder 430 is lowered in this open state. After lowering, the holder 430 is closed and raised while gripping the sample container 2, then returns to the movement start position (mixing position).

The space between the front and rear concavities 441 of the rack holder 410 is set to allow passage of the sample container 2 held by the holder 430. Therefore, when the holder 430 is moved laterally above the rack holder 410 holding the sample container 2, the sample container 2 held by the holder 430 can pass through the space between the sample containers 2 (front and rear space) in the rack 5 set in the front and back concavities 441.

As a result, the holder 430 holding the sample container 2 can be lifted above the rack holder 410 without raising the held sample container 2 to as position higher than the sample container 2 in the rack 5. That is, without raising the holder 430 very much, the holder 430 can be moved above the rack holder 410 while avoiding contact between the held sample container 2 and the sample container 2 in the rack 5.

Thus, the raising height is very slight when moving the holder 430 (movable base 440), such that the operation can be performed quickly and the apparatus can be made more compactly (particularly in the height direction of the apparatus).

Moreover, a sample container sensor 500 is provided to detect whether or not the holder 430 holds a sample container 2 when the holder 430 (movable base 440) holding the sample container 2 returns to the movement start position. If the holder 430 holds a sample container 2, the mixing operation proceeds. When the holder 430 does not hold a sample container 2, the same operation as described above is performed to remove a sample container 2 from the other position of the rack 5.

As shown in FIG. 11, during the mixing operation, the mixing drive unit 460 is rotated to vertically rotate the contact holder 430 to mix the sample within the sample container 2.

When the mixing operation ends, the holder 430 returns to the condition of hanging in a perpendicular direction as shown in FIG. 1.

Then, the holder 430 (movable base 440) holding the sample container 2 holds the sample container 2 in a near vertical state, crosses above the rack holder 410, and moves to a position above the sample container acceptor 310 (receiver 470) astride the rack holder 410.

Then, the holder 430 is lowered, and the sample container 2 is inserted in the sample container receiver 310. Thus, the sample container 2 is set in the sample container receiver 310 in a near vertical upright state. Thereafter, the holder 430 opens, separates from the sample container 2, and is lifted.

Then, the slider 321 is retracted, and the sample container 2 is first positioned at the information reading position (barcode reading position). When the sample container 2 has arrived at the information reading position, the sample container 2 is detected by a sample container sensor 530 provided at the information reading position.

When the sample container 2 arrives at the information reading position, the rotation mechanism 520 rotates the sample container 2, and the information of the information recording area 2b is read by the reader 510 while the sample container is rotated.

After the information has been read, the slider 321 is retracted, and the sample container 2 (sample acceptor 310) is positioned at the aspirating position (refer to the position in FIG. 4) within the sample analyzer main body 3.

The sample of the sample container 2 at the aspirating position is aspirated by the aspirator 330, and measured by the measuring unit. Then the measurement results are analyzed by a computer not shown in the drawing.

When the sample has been aspirated from the sample container 2, the slider 321 advances and the sample container acceptor 310 is again positioned at the receiver 470.

The holder 430 is again lowered to collect the aspirated sample container 2, and the sample container 2 in the sample container acceptor 310 is gripped and lifted. Then, the holder 430 moves to the position of the rack 5, and the sample container 2 is returned to the rack 5.

The holder 430 (movable base 440) returns to the movement start position after the aspirated sample container 5 has been returned to the rack 5.

Thereafter, the same automatic supplying measurement and analysis are performed for the other sample container in the rack 5.

The present invention is not limited to the previously described embodiment and may be variously modified. For example, although two (multiple) racks 5 are disposed with a spacing in front and back in the rack holder 410 in the present embodiment, the number and arrangement of the racks that can be set in the rack holder 410 are not particularly limited. Furthermore, the racks may be automatically supplied to the rack holder 410.

What is claimed is:

1. A sample analyzer for analyzing a sample comprising:
a main body including an analyzing system;
the main body further comprising:
    a sample container acceptor that receives and holds a sample container, the sample container being supplied to the sample container acceptor either manually or automatically;
    an aspirator for aspirating a sample in the sample container at an aspirating position in the main body; and
    a mover having a reciprocating slide plate with the sample container acceptor at a distal end thereof for moving the sample container acceptor from a receiving position outside of the main body to the aspirating position in the main body; and
a sample container supplier comprising:
    a rack holder that receives a rack containing a plurality of sample containers;
    a sample container supplying unit including
        a gripping mechanism coupled to a vertical elevator base that grips the selected sample container and vertically removes the selected sample container from the rack,
        a transport mechanism that transports the selected sample container to the sample container acceptor at the receiving position and
        a rotation mechanism for rotating the sample container held by the sample container acceptor; and
    a reader that reads identifier information provided on the sample container held by the sample container acceptor and is arranged between the receiving position and the main body, wherein the rotation mechanism rotates the selected sample container to bring the selected sample container into proximity with the reader, whereby the reader converts the information into an electronic signal.

2. The sample analyzer according to claim 1, wherein the sample container supplying unit comprises a transmission mechanism that operates to return the selected sample container from the sample container acceptor to the rack after the aspirator has aspirated the sample in the selected sample container.

3. The sample analyzer according to claim 1, wherein the main body further comprises:
    a controller that controls operations of the sample analyzer in a manual mode and an automatic mode, wherein
    in the manual mode, the controller controls the aspirator to aspirate a sample within the sample container, which is manually supplied and held by the sample container acceptor, and,
    in the automatic mode, the controller controls the sample container supplying unit to supply the sample container held by the rack to the sample container acceptor, and the controller also controls the aspirator to aspirate the sample within the sample container held by the sample container acceptor.

4. The sample analyzer according to claim 1, wherein the sample container supplying unit further comprises a rotatable shaft coupled to the gripping mechanism and linkage that engages a drive unit with the rotatable shaft, and wherein the drive unit reciprocally rotates the shaft to mix the sample in the selected sample container in a start position prior to transporting the selected sample container to the sample container acceptor.

* * * * *

UNITED STATES PATENT AND TRADEMARK OFFICE
CERTIFICATE OF CORRECTION

PATENT NO. : 8,158,060 B2
APPLICATION NO. : 11/599790
DATED : April 17, 2012
INVENTOR(S) : Nagai et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 717 days.

Signed and Sealed this
Twenty-first Day of August, 2012

David J. Kappos
*Director of the United States Patent and Trademark Office*